US008723115B2

(12) United States Patent
Xiao et al.

(10) Patent No.: US 8,723,115 B2
(45) Date of Patent: May 13, 2014

(54) METHOD AND APPARATUS FOR DETECTING BURIED DEFECTS

(75) Inventors: Hong Xiao, Pleasanton, CA (US); Ximan Jiang, Milbrae, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/431,659

(22) Filed: Mar. 27, 2012

(65) Prior Publication Data

US 2013/0256528 A1   Oct. 3, 2013

(51) Int. Cl.
*G01N 23/00*   (2006.01)

(52) U.S. Cl.
USPC .......................... 250/307; 250/306; 250/310

(58) Field of Classification Search
None
See application file for complete search history.

(56) References Cited

U.S. PATENT DOCUMENTS

| | | | |
|---|---|---|---|
| 5,504,017 A | | 4/1996 | Yue et al. |
| 5,578,821 A | | 11/1996 | Meisberger et al. |
| 6,217,721 B1 | | 4/2001 | Xu et al. |
| 6,753,525 B1 | | 6/2004 | Testoni |
| 6,777,676 B1 * | | 8/2004 | Wang et al. ...................... 850/8 |
| 6,801,596 B2 | | 10/2004 | Nasser-Ghodsi et al. |
| 6,924,484 B1 | | 8/2005 | Wang et al. |
| 6,996,492 B1 | | 2/2006 | Testoni |
| 7,015,467 B2 * | | 3/2006 | Maldonado et al. ........... 250/306 |
| 7,030,375 B1 * | | 4/2006 | Testoni et al. ................. 250/305 |
| 7,132,652 B1 | | 11/2006 | Testoni |
| 7,202,475 B1 | | 4/2007 | Testoni |
| 7,276,694 B1 * | | 10/2007 | Bertsche ........................ 250/311 |
| 7,425,701 B2 | | 9/2008 | Steigerwald et al. |
| 7,446,474 B2 * | | 11/2008 | Maldonado et al. ........... 313/542 |
| 7,507,962 B2 | | 3/2009 | Steigerwald et al. |
| 7,643,611 B2 | | 1/2010 | Shedlock et al. |
| 7,714,287 B1 | | 5/2010 | James et al. |
| 7,855,159 B1 | | 12/2010 | Yeckley |
| 7,910,887 B2 | | 3/2011 | Steigerwald et al. |
| 8,045,145 B1 * | | 10/2011 | Bakker et al. ............... 356/237.2 |
| 8,368,018 B2 * | | 2/2013 | Hatakeyama et al. ........ 250/310 |
| 2001/0016938 A1 * | | 8/2001 | Nishiyama et al. ............. 716/21 |
| 2002/0036272 A1 | | 3/2002 | Okino |

(Continued)

FOREIGN PATENT DOCUMENTS

| | | | |
|---|---|---|---|
| EP | 0 799 903 A2 | 10/1997 | |
| EP | 2 312 302 A1 | 4/2011 | |

(Continued)

OTHER PUBLICATIONS

PCT International Search Report and Written Opinion of the International Searching Authority for Application No. PCT/US2013/033771, Jul. 23, 2013, 8 sheets.

*Primary Examiner* — Andrew Smyth
(74) *Attorney, Agent, or Firm* — Okamoto & Benedicto LLP

(57) ABSTRACT

One embodiment relates to a method of detecting a buried defect in a target microscopic metal feature. An imaging apparatus is configured to impinge charged particles with a landing energy such that the charged particles, on average, reach a depth within the target microscopic metal feature. In addition, the imaging apparatus is configured to filter out secondary electrons and detect backscattered electrons. The imaging apparatus is then operated to collect the backscattered electrons emitted from the target microscopic metal feature due to impingement of the charged particles. A backscattered electron (BSE) image of the target microscopic metal feature is compared with the BSE image of a reference microscopic metal feature to detect and classify the buried defect. Other embodiments, aspects and features are also disclosed.

14 Claims, 3 Drawing Sheets

(56) References Cited

U.S. PATENT DOCUMENTS

| | | |
|---|---|---|
| 2002/0036273 A1 | 3/2002 | Okino |
| 2003/0094572 A1* | 5/2003 | Matsui et al. ............... 250/310 |
| 2003/0204826 A1* | 10/2003 | Nishiyama et al. ............ 716/4 |
| 2003/0206292 A1* | 11/2003 | Some ....................... 356/237.1 |
| 2004/0140432 A1* | 7/2004 | Maldonado et al. ....... 250/423 P |
| 2005/0087686 A1* | 4/2005 | Honda et al. ................. 250/307 |
| 2006/0055321 A1* | 3/2006 | Maldonado et al. .......... 313/527 |
| 2006/0267012 A1* | 11/2006 | Maegawa et al. ............... 257/57 |
| 2007/0230768 A1* | 10/2007 | Adler et al. .................... 382/144 |
| 2008/0099675 A1* | 5/2008 | Hiroi et al. .................... 250/307 |
| 2008/0246030 A1* | 10/2008 | Satya et al. ..................... 257/48 |
| 2009/0090863 A1* | 4/2009 | Watanabe et al. ............. 250/307 |
| 2009/0314937 A1 | 12/2009 | Sellmair |
| 2010/0019147 A1* | 1/2010 | Hatakeyama et al. ........ 250/307 |
| 2010/0093022 A1 | 4/2010 | Hayworth et al. |
| 2010/0243888 A1 | 9/2010 | Nishiyama et al. |
| 2011/0036981 A1* | 2/2011 | Zhao et al. ..................... 250/307 |
| 2011/0155905 A1 | 6/2011 | Hatakeyama et al. |
| 2012/0233542 A1* | 9/2012 | Funakoshi ..................... 715/243 |
| 2012/0292502 A1* | 11/2012 | Langer et al. ................. 250/307 |

FOREIGN PATENT DOCUMENTS

| | | |
|---|---|---|
| JP | 11-160247 A | 6/1999 |
| JP | 2006-286685 A | 10/2006 |
| JP | 2010-255059 A | 11/2010 |
| KR | 10-2008-0030315 A | 4/2008 |
| WO | 2008066846 A2 | 6/2008 |
| WO | 2008100654 A2 | 8/2008 |
| WO | 2008134757 A1 | 11/2008 |

* cited by examiner

FIG. 1                    100

METHOD AND APPARATUS FOR DETECTING BURIED DEFECTS

BACKGROUND OF THE INVENTION

1. Field of the Invention

The present invention relates to methods and apparatus for inspection and/or review of semiconductor wafers and other manufactured substrates.

2. Description of the Background Art

Semiconductor manufacturing involves various processes. Common processes include those that form microscopic features on the substrate being manufactured. The microscopic features may comprise dielectric or metallic materials, for example.

Microscopic metal features may include plugs and lines and may be formed by dielectric etch, metal deposition and metal chemical mechanical polishing (CMP) processes. The detection of voids in such metal features is generally an issue of interest in integrated circuit chip manufacturing. However, detecting voids or other buried defects in microscopic metal features, particularly in metal plugs and other features that are less than a micron in width, is a very challenging task due to the hidden nature of these defects.

SUMMARY

One embodiment relates to a method of detecting a buried defect in a target microscopic metal feature. An imaging apparatus is configured to impinge charged particles with a landing energy such that the charged particles, on average, reach a depth within the target microscopic metal feature. In addition, the imaging apparatus is configured to filter out secondary electrons and detect backscattered electrons. The imaging apparatus is then operated to collect the backscattered electrons emitted from the target microscopic metal feature due to impingement of the charged particles. A backscattered electron (BSE) image of the target microscopic metal feature is compared with the BSE image of a reference microscopic metal feature to detect and classify the buried defect.

Another embodiment relates to an apparatus configured to detect a buried defect in a target microscopic metal feature. The apparatus includes at least a charged-particle beam column, a detector, and a data processing system. The charged-particle beam column is configured to generate an incident beam of charged particles. The landing energy of the incident beam is at a level such that the charged particles, on average, reach a depth of interest, where the depth of interest is below the surface but less than a maximum depth of the buried defect. The detector is configured to filter out secondary electrons and detect backscattered electrons. The data processing system is configured to compare a backscattered electron (BSE) image of the target microscopic metal feature with the BSE image of a reference microscopic metal feature to detect and classify the buried defect.

In alternate embodiments, the above-described method and apparatus may be applied to detect buried defects in dielectric features, rather than metal features. Other embodiments, aspects and features are also disclosed.

DETAILED DESCRIPTION

One conventional technique for detecting voids in microscopic metal features involves using a test structure and electrical probing. The electrical probing is generally performed after formation of a metal layer which interconnects to the test structure. Unfortunately, the electrical probing technique is not capable of detecting voids in the metal features before metal layer formation. Furthermore, the electrical probing technique may only detect voids in the test structure and generally not in devices outside of the test structure. This substantially limits the use of this technique.

Traditional electron beam imaging (EBI) has some capability to detect voids in thin dielectric films. However, traditional EBI has so far been unable to reliably detect voids in microscopic metal plugs and lines. Such detection may be particularly difficult for metal features that are less than a micron in width.

As disclosed herein, applicants have determined a method and apparatus which may be used to effectively detect voids and/or volume variations buried in microscopic metal features. The method and apparatus may be applied to metal features that are less than a micron in width.

The method disclosed herein involves using both a high landing energy which is above 3.1 keV and a detection configuration that filters out secondary electrons so as to detect backscattered electrons in an isolated manner. The apparatus disclosed herein includes an electron beam column with applied voltages set to provide for a high landing energy which is above 3.1 keV and with a detector configured to detect the backscattered electrons while filtering out secondary electrons. For both the method and the apparatus, the high landing energy used may be 6 keV or higher, for example.

Advantageously, the presently-disclosed method and apparatus may be used to detect voids in metal plugs, such as tungsten plugs in a static random access memory (SRAM) array, for example. Previously, such voids were only detected by an electrical probing test at the end of an integrated circuit (IC) chip fabrication process. The presently-disclosed method and apparatus enables IC manufacturers to advantageously detect such yield-reducing defects at a much earlier stage in the manufacturing process flow. For example, the presently-disclosed technique to detect buried defects may be applied after the step of chemical mechanical polishing of tungsten (or copper) features.

Figure 1:
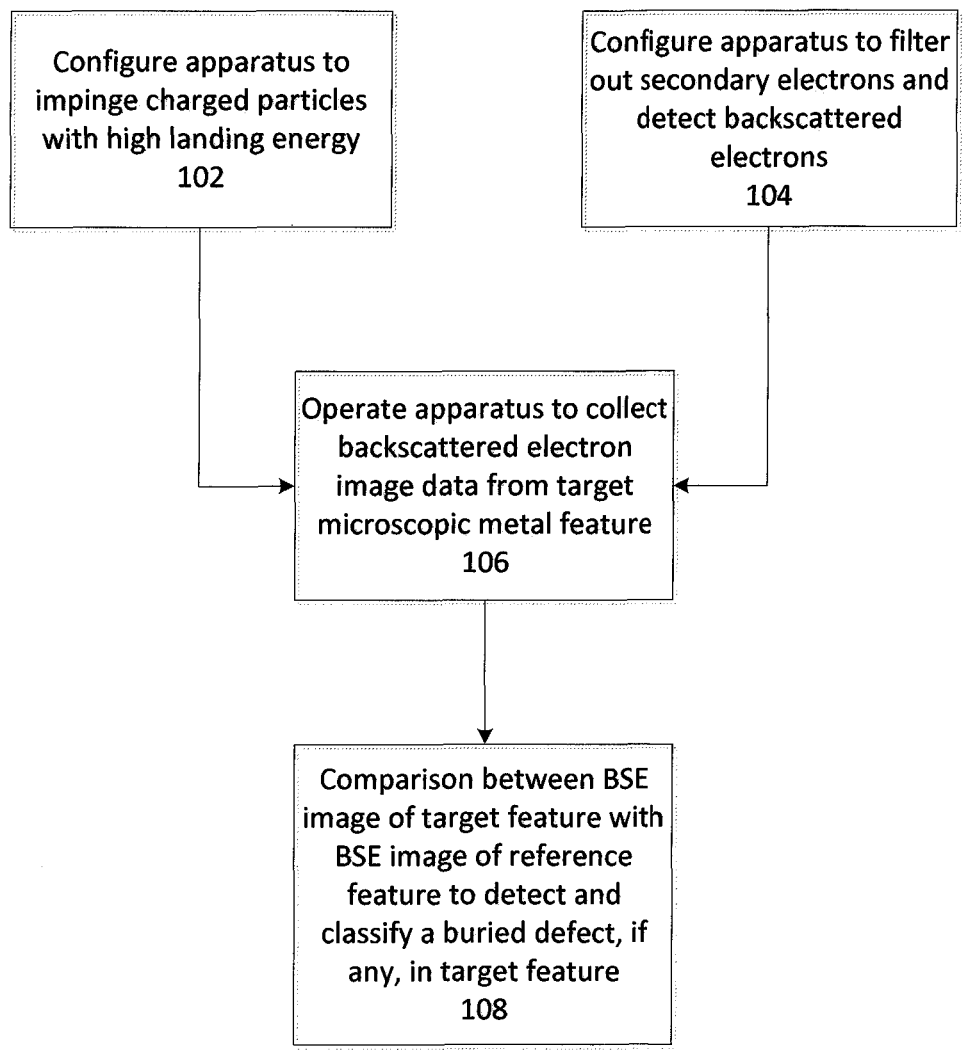
FIG. 1 is a flow chart of a method for detecting buried defects in microscopic metal features in accordance with an embodiment of the invention.

FIG. 1 is a flow chart of a method 100 for detecting buried defects in microscopic metal features in accordance with an embodiment of the invention. The metal features may include metal plugs and metal lines formed on a semiconductor substrate during an integrated circuit manufacturing process. The buried defects may include voids and undesired volume variations.

As shown, the method 100 begins by configuring a charged-particle imaging apparatus as indicated by blocks 102 and 104. In one embodiment, the charged-particle imaging apparatus may be an electron beam imaging apparatus such as the EBI apparatus 200 depicted in FIG. 2.

Per block 102, the apparatus may be configured to impinge the charged particles onto the target substrate with a high landing energy. For example, using the EBI apparatus 200 of FIG. 2, the system controller and data processing system 240 may control the operating voltage 252 applied at the electron gun 202 to control the bias voltage 254 applied to the stage 223. The landing energy is generally proportional to the difference between the operating voltage 252 and the bias voltage 254.

The high landing energy should be sufficiently high such that the charged particles, on average, will reach a depth of interest below the surface. The depth of interest is a depth below the surface which is desired to be inspected for defects. For example, using the apparatus 200 of FIG. 2 on a target feature composed primarily of tungsten, the operating voltage 252 and the bias voltage 254 may be controlled such that the landing energy is above 3.1 keV so that the incident electrons will, on average, penetrate to a depth of interest below the surface of the tungsten feature. For instance, the landing energy to inspect a tungsten feature may be 6 keV or higher.

Per block 104, the apparatus may be configured to filter out secondary electrons and detect backscattered electrons in the scattered electron beam 205. For example, using the EBI apparatus 200 of FIG. 2, a high negative potential may be applied to one or more energy filters (see 225 and 226, for example) in the path of the scattered electron beam 205 such that only the backscattered electrons will have sufficient energy to reach the detector 228. Alternatively, other energy filtering techniques may be used. For example, an energy-dependent dispersive device, such as Wien filter 218, may be used in combination with a position-sensitive detector to filter the electrons so as to filter out the secondary electrons while detecting the backscattered electrons.

Per block 106, after the apparatus is configured per blocks 102 and 104, the apparatus may be operated to collect backscattered image data from the target microscopic metal feature. For example, using the EBI apparatus 200 of FIG. 2, the incident electron beam 203 may be scanned over an area of the target substrate 222, where the scanned area includes the target feature. Backscattered electrons may then be detected by the detector 228 such that BSE image data of the target feature may be generated and stored.

Per block 108, a comparison may be made between a BSE image of the target feature and a BSE image of a corresponding reference feature so as to detect and classify buried defects, if any, in the target feature. The reference feature is a feature that is known to be a normal (non-defective) feature. The target and reference features are corresponding in that they are designed to have the same dimensions and material properties. The BSE images of the target and reference features should be obtained using the same configuration for the imaging apparatus (for example, same beam intensity, same landing energy, and so on). The image comparison for defect detection and classification may be performed, for example, by the system controller and data processing system 240 of FIG. 2.

In accordance with an embodiment of the invention, the image comparison may involve comparing a grey level of pixels in the target feature with the grey level of corresponding pixels in the reference feature. A distribution of the location of the lower grey level pixels may also be determined during the image comparison.

In one example, if the grey level of pixels of the target tungsten plug is substantially lower such that the difference in grey levels is above a threshold difference, then the target metal plug may be deemed to have a defect in that it has less tungsten material buried under the surface. The classification of the defect may be determined based, for example, on the landing energy used to obtain the images and also on the distribution of the lower grey level pixels. Examples of particular buried defects that may be detected and classified using this method 100 are discussed below in relation to FIG. 3.

Figure 2:
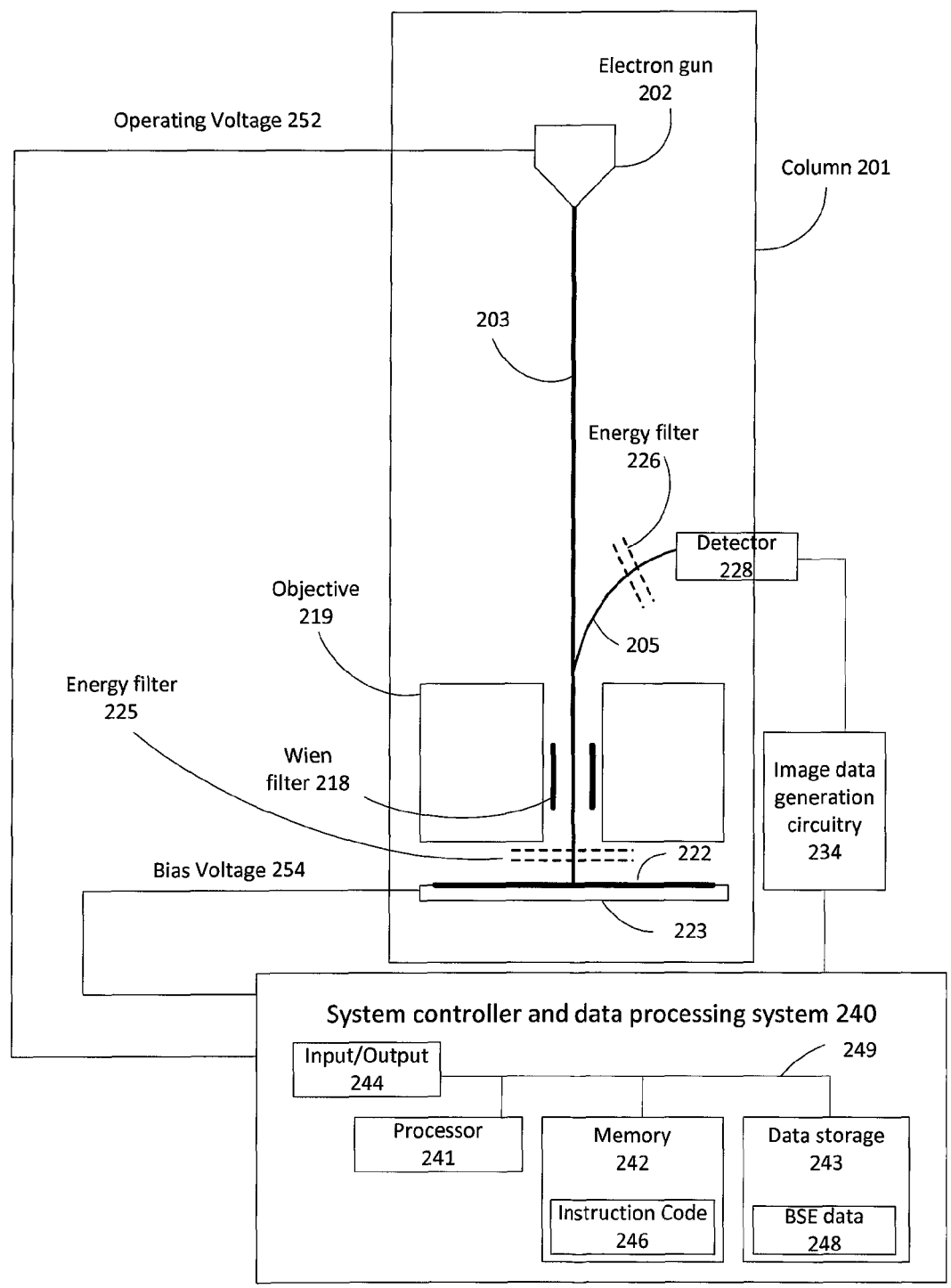
FIG. 2 is a block diagram depicting a cross-sectional view of an example electron beam imaging apparatus which may be configured for detecting buried defects in microscopic metal features in accordance with an embodiment of the invention.

FIG. 2 is a diagram depicting a cross-sectional view of an example electron beam imaging apparatus 200 which may be configured for detecting buried defects in microscopic metal features in accordance with an embodiment of the invention. Note that FIG. 2 depicts select components and features of an example implementation of such an apparatus. The apparatus 200 may also include various other components and features which are not shown.

As shown in FIG. 2, the apparatus 200 may include an electron beam column 201 which has an electron gun 202. An incident electron beam 203 is generated by the electron gun 202 and focused by one or more electron lenses in the column 201 onto a beam spot on a surface of the target substrate 222. The target substrate 222 may be held by a movable stage 223.

The landing energy of the incident electrons is generally determined by the operating voltage 252 applied to the electron gun 202 and the bias voltage 254 applied to the stage 223 which holds the target substrate 222. The bias voltage 254 is also typically applied to the objective lens 219. These applied voltages may be generated by high-voltage power supplies under control of the system controller and data processing system 240. In accordance with an embodiment of the invention, the operating voltage 252 and the bias voltage 254 may be controlled such that the landing energy is above 3.1 eV. For example, the landing energy may be 6 keV or higher when the target feature is composed of tungsten.

The apparatus 200 also includes a detection system which may be arranged to selectively detect electrons 205 in a controllable range of energies from the electrons emitted from the target substrate 222. In general, the electrons emitted from the target substrate 222 may include both secondary electrons and backscattered electrons. However, in accordance with an embodiment of the present invention, the detection system may be arranged so as to selectively detect the backscattered electrons while filtering out the secondary electrons.

In the example implementation shown in FIG. 2, one or more energy filters may be arranged in the path of the scattered electron beam 205. For example, in the embodiment illustrated in FIG. 2, a first energy filter 225 is arranged between the target substrate 222 and the objective lens 219, and a second energy filter 226 is arranged in front of the detector 228. A sufficiently high negative potential may be applied to the energy filter such that only the backscattered electrons will have sufficient energy to pass through and eventually reach the detector 228. This is because the backscattered electrons typically have a much higher energy value than the secondary electrons. In an alternate embodiment, instead of (or in addition to) using one or more energy filters, an energy-dependent dispersive device may be used in combination with a position-sensitive detector to filter the electrons so as to filter out the secondary electrons while detecting the backscattered electrons.

Once the electrons are detected by the detector 228, the detected signal may be received and processed by image data generation circuitry 234 (which may include, for example, analog-to-digital conversion circuitry and frame buffers). The image data generated by the image data generation circuitry 234 may be provided to the system controller and data processing system 240.

A simplified block diagram showing select components of the system controller and data processing system 240 is depicted in FIG. 2. As shown, the system controller and data processing system 240 may include a processor 240, memory 242, a data storage system 243, input/output interfaces 244, and a communication system 249 which communicatively interconnects the aforementioned components. The processor 240 may be configured to execute computer-readable instructions that may be stored in the memory 242. The data storage system 243 may be configured to stores instructions and data in a non-transitory manner on a computer-readable medium. The input/output interfaces 244 may be configured to communicate data with external components or systems.

As shown, in accordance with an embodiment of the invention, the memory 242 may be configured to hold instruction code 246 which may be executed by the processor 241. In accordance with an embodiment of the invention, the instruction code 246 may be configured so as to implement the method 100 described above in relation to FIG. 1.

As further shown, the data storage 243 may be configured to store BSE image data (BSE data) 248 from the image data generation circuitry 234. The BSE data 248 may include target and reference BSE image data. The target and reference BSE image data may be utilized to generate difference images so as to detect buried defects as described above in relation to FIG. 1.

Figure 3:
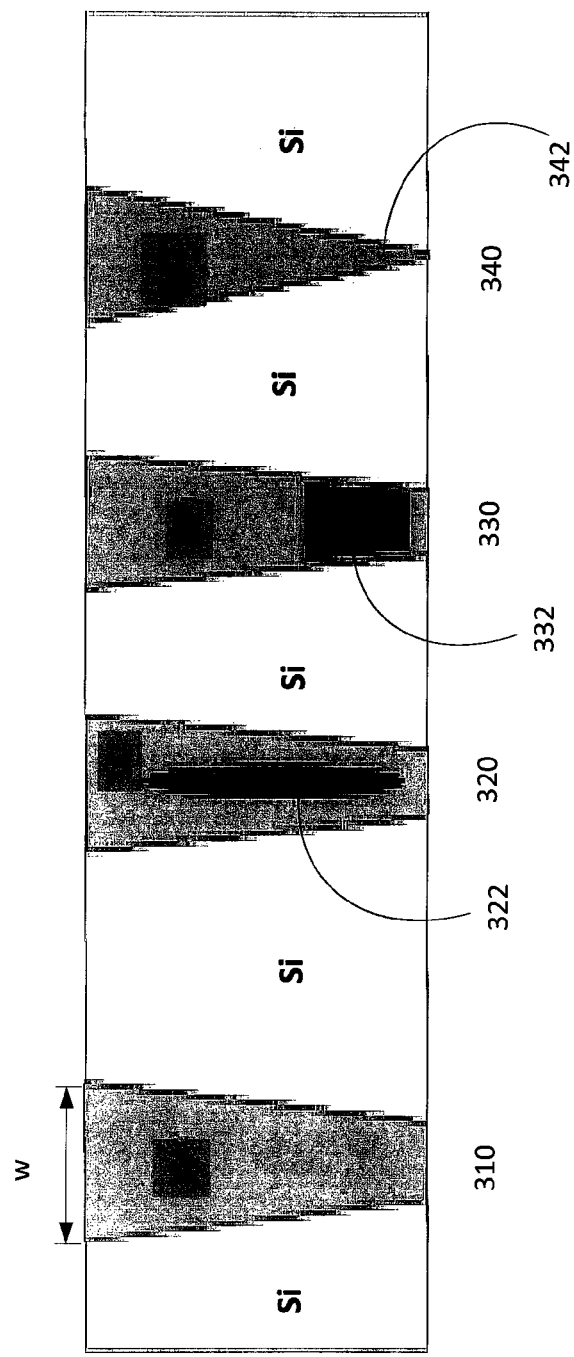
FIG. 3 is an illustrative cross-sectional diagram showing tungsten plugs and examples of buried defects therein that may be detected by the method and apparatus disclosed herein.

FIG. 3 is an illustrative cross-sectional diagram showing tungsten (W) plugs and examples of buried defects therein that may be detected by the method and apparatus disclosed herein. Shown in the figure are cross sections of several tungsten plugs in a silicon (Si) layer, including a normal (non-defective) tungsten plug 310 and three tungsten plugs (320, 330, and 340) with buried defects.

The leftmost tungsten plug 310 is a normal (non-defective) plug with a width w at the surface. Such tungsten plugs are often less than a micron in width in current semiconductor manufacturing processes. Buried defects within such tungsten plugs and similar metal features are difficult to detect with conventional techniques. However, the presently-disclosed method and apparatus may be used to effectively detect such below-surface defects in tungsten plugs and lines, copper plugs and lines, and similar metal features.

The next tungsten plug 320 is a first example of a feature which has a buried defect that may be detected using the presently-disclosed method and apparatus. In this case, the plug 320 has a seam void 322 buried under the surface.

The next tungsten plug 330 is a second example of a feature which has a buried defect that may be detected using the presently-disclosed method and apparatus. In this case, the plug 330 has a hollowed bottom 332 buried under the surface.

The rightmost tungsten plug 340 is a third example of a feature which has a buried defect that may be detected using the presently-disclosed method and apparatus. In this case, the plug 340 has a pinched bottom 342 buried under the surface.

Detecting the hollowed bottom 332 and pinched bottom 342 defects may require obtaining the target and reference BSE image data at a higher landing energy than the landing energy needed to detect a seam void 322. This is because the hollowed bottom 332 and the pinched bottom 342 are buried further under the surface than the seam void 322.

Hence, if the landing energy is at a level such that the incident charged particles will on average reach a middle depth of a plug, and lower grey level pixels are found in the center region of the target plug, then comparison block 108 in the buried defect detection method 100 may determine that the defect is to be classified as a seam void 322. On the other hand, if the landing energy is at a level such that the incident charged particles will on average reach a depth near a bottom of a plug, and lower grey level pixels are found in the center region of the target plug, then comparison block 108 in the buried defect detection method 100 may determine that the defect is to be classified as a hollow bottom 332.

A hollowed bottom 332 may be differentiated from a pinched bottom 342 by determining the distribution in the locations of the lower grey level pixels in the target BSE image. Hence, if the landing energy is at a level such that the incident charged particles will on average reach a depth near a bottom of a plug, and the lower grey level pixels in the target BSE image are located in a center region of the target plug, then the comparison block 108 may determine that the defect is to be classified as a hollowed bottom 332. On the other hand, if the landing energy is at a level such that the incident charged particles will on average reach a depth near a bottom of a plug, and the lower grey level pixels in the target BSE image are located in an annular region of the target feature, then the comparison block 108 may determine that the defect is to be classified as a pinched bottom 342.

Other defects in plugs that may be detected using the presently-disclosed method and apparatus include a half-filled plug and metal plug volume variation that may be induced by contact hole profile variation. The presently-disclosed method and apparatus may also detect buried defects in metal lines.

While the above description focuses on detecting buried defects in metal features, the method and apparatus disclosed herein may also be used to detect buried defects in dielectiric features. For example, voids in a dielectric layer, such as a shallow trench isolation (STI) layer or an inter-layer dielectric, may be detected.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. An apparatus configured to detect a buried defect in a target microscopic metal feature, the apparatus comprising:
    a charged-particle beam column configured to generate an incident beam of charged particles, wherein the landing energy is at a level such that the charged particles, on average, reach a depth of interest, and the depth of interest is less than a maximum depth of the buried defect;
    a detector configured to filter out secondary electrons and detect backscattered electrons; and
    a data processing system configured to compare a backscattered electron (BSE) image of the target microscopic metal feature with the BSE image of a reference microscopic metal feature to detect and classify the buried defect, wherein the data processing system is further configured, if said target feature is a plug, to classify the buried defect as a hollow bottom if pixels in a middle region of said target microscopic metal feature have lower grey levels when compared against pixels in the middle region of said reference microscopic metal feature, and classify the buried defect as a pinched bottom if pixels in an annular region of said target microscopic metal feature have lower grey levels when compared against pixels in the annular region of said reference microscopic metal feature.

2. The apparatus of claim 1, wherein the target microscopic metal feature comprises tungsten.

3. The apparatus of claim 1, wherein the target microscopic metal feature comprises copper.

4. The apparatus of claim 1, wherein the charged particles are electrons.

5. The apparatus of claim 1, wherein the secondary electrons are filtered out using an energy filter in the detection system.

6. The apparatus of claim 1, wherein the landing energy is greater than 3.1 kilo electron-volts.

7. The apparatus of claim 1, wherein the landing energy is greater than 6 kilo electron-volts.

8. A method of detecting a buried defect in a target microscopic metal feature, the method comprising:
   configuring an imaging apparatus to impinge charged particles with a landing energy such that the charged particles, on average, reach a depth within the target microscopic metal feature;
   configuring the imaging apparatus to filter out secondary electrons and detect backscattered electrons;
   operating the imaging apparatus to collect the backscattered electrons emitted from the target microscopic metal feature due to impingement of the charged particles; and
   comparing a backscattered electron (BSE) image of the target microscopic metal feature with the BSE image of a reference microscopic metal feature to detect and classify the buried defect;
   wherein if said target feature is a plug, the buried defect is classified as a hollow bottom if pixels in a middle region of said target microscopic metal feature have lower grey levels when compared against pixels in the middle region of said reference microscopic metal feature, and the buried defect is classified as a pinched bottom if pixels in an annular region of said target microscopic metal feature have lower grey levels when compared against pixels in the annular region of said reference microscopic metal feature.

9. The method of claim 8, wherein the buried defect comprises a void in the microscopic metal feature.

10. The method of claim 9, wherein the buried defect is classified as a void due, at least in part, to pixels in a middle region of said target feature having lower grey levels when compared against pixels in the middle region of said reference feature.

11. The method of claim 8, wherein the target microscopic metal feature comprises a tungsten feature.

12. The method of claim 8, wherein the target microscopic metal feature comprises a copper feature.

13. The method of claim 8, wherein the landing energy is greater than 3.1 kilo electron-volts.

14. The method of claim 8, wherein the landing energy is greater than 6 kilo electron-volts.

* * * * *